United States Patent
Bornzin et al.

(10) Patent No.: US 6,766,195 B1
(45) Date of Patent: Jul. 20, 2004

(54) METHOD AND APPARATUS FOR DETECTING NATURAL ELECTRICAL COHERENCE WITHIN THE HEART AND FOR ADMINISTERING THERAPY BASED THEREON

(75) Inventors: Gene A. Bornzin, Simi Valley, CA (US); Peter Boileau, Valencia, CA (US); Joseph J. Florio, La Canada, CA (US); John W. Poore, South Pasadena, CA (US); Kelly H. McClure, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 334 days.

(21) Appl. No.: 09/686,630

(22) Filed: Oct. 10, 2000

Related U.S. Application Data
(60) Provisional application No. 60/173,341, filed on Dec. 28, 1999.

(51) Int. Cl.[7] ............................................. A61N 01/18
(52) U.S. Cl. ................................ 607/14; 607/4; 607/5; 600/515
(58) Field of Search ........................ 607/4, 5; 600/513, 600/515, 518, 519, 526

(56) References Cited

U.S. PATENT DOCUMENTS

| | | | | |
|---|---|---|---|---|
| 5,107,850 A | | 4/1992 | Olive | 128/705 |
| 5,158,092 A | * | 10/1992 | Glace | 600/518 |
| 5,193,550 A | * | 3/1993 | Duffin | 128/697 |
| 5,466,254 A | | 11/1995 | Helland | 607/123 |
| 5,697,954 A | * | 12/1997 | Sears et al. | 607/5 |
| 5,718,242 A | * | 2/1998 | McClure et al. | 128/704 |
| 5,741,304 A | * | 4/1998 | Patwardhan et al. | 607/5 |
| 5,840,079 A | | 11/1998 | Warman et al. | 607/4 |
| 5,868,680 A | * | 2/1999 | Steiner et al. | 600/518 |
| 6,078,837 A | | 6/2000 | Peterson et al. | 607/14 |
| 6,081,746 A | | 6/2000 | Pendekanti et al. | 607/5 |
| 6,085,116 A | | 7/2000 | Pendekanti et al. | 607/5 |
| 6,308,095 B1 | * | 10/2001 | Hsu et al. | 600/518 |
| 6,415,179 B1 | | 7/2002 | Pendekanti et al. | 607/5 |

FOREIGN PATENT DOCUMENTS

| | | | | |
|---|---|---|---|---|
| EP | 0748638A2 A3 | | 12/1996 | A61N/1/368 |
| WO | WO 95/28988 | | 11/1995 | A61N/1/39 |

* cited by examiner

*Primary Examiner*—Mark Bockelman

(57) ABSTRACT

Techniques are provided for detecting natural electrical coherence within the heart and for administering or adjusting therapy based upon whether natural electrical coherence is detected. In one example, an implantable cardioverter defibrillator (ICD), upon detecting atrial fibrillation, delays administering an atrial defibrillation pulse until a period of natural electrical coherence is detected between the left and the right atria of the heart. The ICD may further delay the pulse until the ventricles of the heart are refractory so as to help prevent triggering ventricular fibrillation. The pulses are administered at a time selected based upon the period of electrical coherence to reduce the amount of electrical energy required within the pulse to reliably defibrillate the heart. Other types of therapy besides defibrillation therapy such as anti-tachycardia pacing pulses may also be timed based upon detection periods of natural electrical coherence. Method and apparatus embodiments are described.

15 Claims, 8 Drawing Sheets

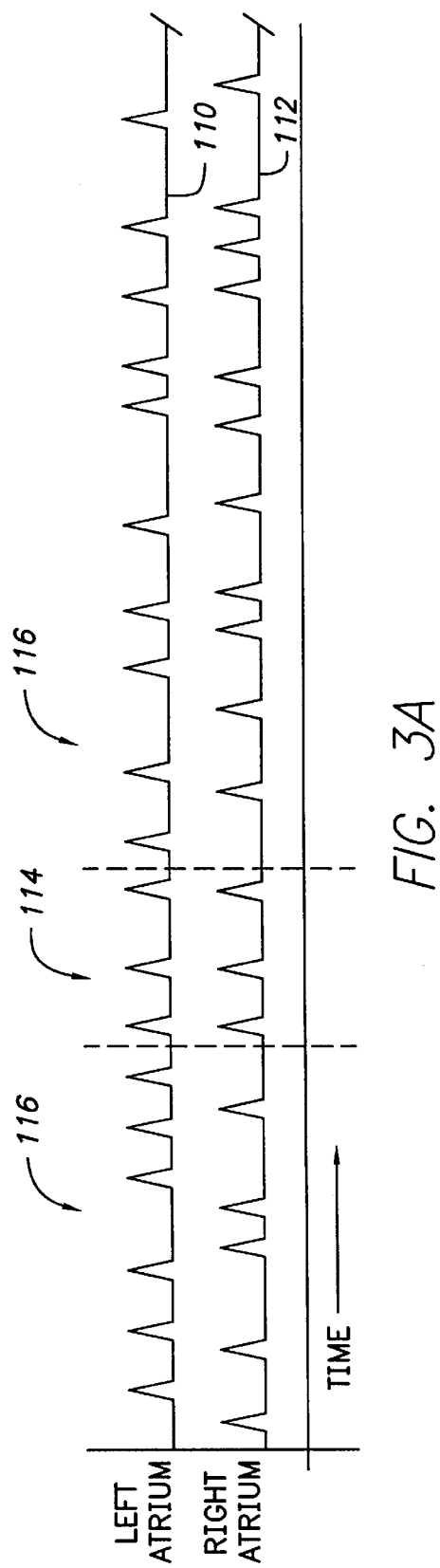

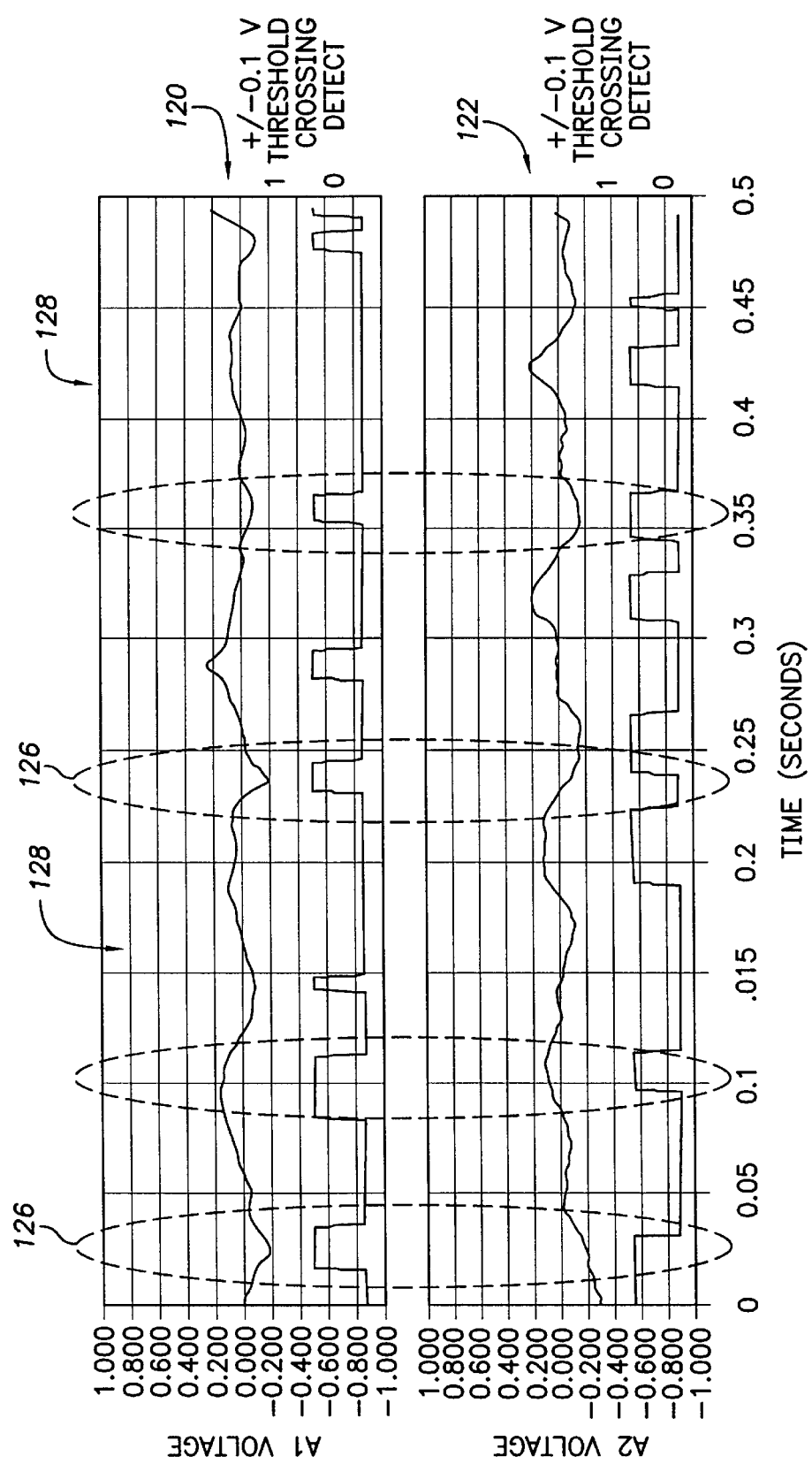

METHOD AND APPARATUS FOR DETECTING NATURAL ELECTRICAL COHERENCE WITHIN THE HEART AND FOR ADMINISTERING THERAPY BASED THEREON

This application claims the benefit of U.S. Provisional Application No. 60/173,341, filed Dec. 28, 1999.

FIELD OF THE INVENTION

The invention generally relates to techniques for analyzing the electrical activity of the heart and for administering electrical therapy to the heart.

BACKGROUND OF THE INVENTION

Atrial fibrillation ("AF") is a heart arrhythmia wherein the atria of the heart beat chaotically thereby providing generally poor conduction of blood into the ventricles of the heart and hence reducing the flow of blood throughout the body. AF, by itself, is typically not fatal. However, AF has been shown to lead to long term health problems such as increased risk of thrombolytic stroke. AF can also cause reduced cardiac efficiency, irregular ventricular rhythm and unpleasant symptoms such as palpitations and shortness of breath.

Hence, it is highly desirable to terminate AF. One technique for terminating AF is to administer an electrical cardioversion pulse to the atria of the heart. The cardioversion pulse, if successful, terminates the chaotic pulsing of the atria and causes the atria to resume a normal beating pattern. In an attempt to insure success, the amount of electrical energy in the cardioversion pulse is set to an amount greater than an atrial defibrillation threshold ("DFT") which represents the minimum amount of energy that typically needs to be applied to the heart to terminate AF. The atrial DFT may vary from patient to patient. To determine the atrial DFT for a particular patient, AF is typically induced within the patient, then cardioversion pulses of varying strengths are applied to determine an amount of energy that can reliably defibrillate the atria of the particular patient.

Patients prone to AF may have an implantable cardioverter defibrillator ("ICD") implanted therein capable of detecting AF and automatically administering one or more cardioversion pulses to terminate the AF. The atrial DFT for the patient is programmed into the ICD so that a controller of the ICD can determine the appropriate amount of electrical energy to administer within each cardioversion pulse. Typically, about two joules of energy is administered within each pulse. A typical ICD is also capable of detecting a wide variety of other heart disrythmias, such as ventricular fibrillation (VF), and for administering appropriate therapy as well. For VF, the ICD administers a stronger defibrillation pulse sufficient to overcome a ventricular DFT, on the order of ten to twelve joules of electrical energy, directly to the ventricles of the heart.

Although cardioversion pulses have been found to be effective for terminating AF and other atrial tachyarrhythmias within many patients, the cardioversion pulses can be quite painful to the patient. One reason the cardioversion pulses are painful is that the patient is typically conscious and alert at the time the pulse is administered. In contrast, the much stronger defibrillation pulse for terminating VF is typically not administered until the patient has lost consciousness and hence the patient may feel only residual chest pain upon being revived. Because AF is not usually immediately life-threatening, painful shocks for its treatment may be perceived by patients as worse than the disease itself and therefore not tolerated.

Thus, it is highly desirable to provide a technique for reducing the strength of the electrical cardioversion shock to thereby reduce the amount of pain induced in the patient, while still providing a sufficient amount of electrical energy to reliably defibrillate the atria of the heart. Another significant advantage of reducing the electrical energy per cardioversion pulse is that the lifetime of the power supply of the ICD is thereby significantly increased.

It has been found that certain shocking electrode locations and cardioversion waveforms lead to decreased atrial DFT's. To prevent the cardioversion pulse from inadvertently triggering a VF, the cardioversion pulse is timed so as to occur during a ventricular refractory period occurring immediately subsequent to a contraction within the ventricles. To this end, the ICD also examines the IEGM to detect R-waves representative of contractions within the ventricles and times the application of the cardioversion pulse to occur during the ventricular refractory period.

Another method of cardioversion employs a train of sequential discrete pulses each having a considerably lower energy level than a single cardioversion pulse. Although these various techniques are helpful in reducing the amount of electrical energy per cardioversion pulse, considerable room for improvement remains.

Many of the concerns arising with respect to administering cardioversion pulses to terminate AF also apply to administering cardioversion pulses to terminate ventricular tachyarrhythmias. Heretofore, most techniques, which attempt to reduce the energy per cardioversion pulse are directed to selecting an optimum location for electrodes employed in administering the pulse. Other techniques have been directed to selecting optimal cardioversion waveforms.

For at least the foregoing reasons, it is highly desirable to provide techniques for reducing the strength of atrial and ventricular cardioversion pulses, particularly defibrillation pulses, while still achieving a high likelihood of success, and aspects of invention are directed to these ends.

Insofar as other forms of electrical cardiac therapy are concerned, such as anti-bradycardia pacing, a reduction in the strength of the electrical therapy while still achieving a high likelihood of success is also beneficial. Accordingly, aspects of the invention are also directed to permitting a reduction in the strength of other forms of electrical cardiac therapy besides cardioversion therapy.

SUMMARY OF THE INVENTION

In accordance with one aspect of the invention, a method is provided for applying an electrical pulse to a heart using an implantable cardiac stimulating device connected to the heart for terminating atrial fibrillation within the heart, wherein the pulse is applied based upon detection of a period of natural electrical coherence in the atria.

In accordance with the method, atrial fibrillation is detected within the heart. Then, a period of natural electrical coherence is detected among a plurality of separate locations within the atria of the heart. An electrical pulse is generated for applying to the heart at a time selected based upon the period of natural electrical coherence. Some of the plurality of locations may be, for example, within the left atria whereas others are within the right atria. As another example, the plurality of locations all may be within the left atria, but located separately from one another. The pulse may be applied, for example, during the period of electrical coherence, immediately after the period, or only after several consecutive periods of coherence have been detected. In any case, it is believed that the strength of the cardioversion pulse can be reduced as compared to pulses administered without regard to natural electrical coherence, while still achieving the same likelihood of successful cardioversion.

In accordance with another aspect of the invention, a method is provided for analyzing the electrical activity of the heart using an implantable medical device connected to a heart. In accordance with the method, electrical signals are detected at a plurality of locations within the heart. The electrical signals are compared to identify one or more periods of natural electrical coherence among the signals. Some of the plurality of locations may be, for example, within the left atrium of the heart whereas others are within the right atrium.

In an exemplary embodiment, wherein the implantable medical device includes a cardiac stimulating device, therapy is then selectively administered to the heart at a time based upon detection of the period of natural electrical coherence. The electrical therapy may be, for example, atrial or ventricular cardioversion therapy or pacing therapy. By administering therapy based upon detection of natural electrical coherence, it is believed that the therapy can be more effective.

Apparatus embodiments of the invention are also provided. Other objects, advantages and features of the invention are either specifically described below or will be apparent from the descriptions which follow and from the drawings provided herewith.

BRIEF DESCRIPTION OF THE DRAWINGS

FIG. 3A illustrates $F_A$-waves in left and right atrial IEGM signals and periods of coherence therebetween.

FIG. 3B illustrates left and right atrial IEGM signals detected during atrial fibrillation and periods of coherence therebetween.

DETAILED DESCRIPTION OF THE INVENTION

With reference to the figures, exemplary and preferred implementations of the invention will now be described. Briefly, the invention relates to techniques for detecting periods of natural electrical coherence within the heart and or administering therapy to the heart at time periods based upon detection of coherence so as to permit more effective therapy. The invention will be described primarily with reference to the defibrillation of the heart by an ICD during an episode of AF or VF. However, principles of the invention are applicable to other circumstances wherein detection of natural electrical coherence of the heart can be exploited, such as for use in applying other types of electrical therapy to remedy other dysrhythmias such as ventricular tachycardia and atrial flutter. Principles of the invention can also be exploited by other implantable medical devices, such as pacemakers and the like.

Figure 1:
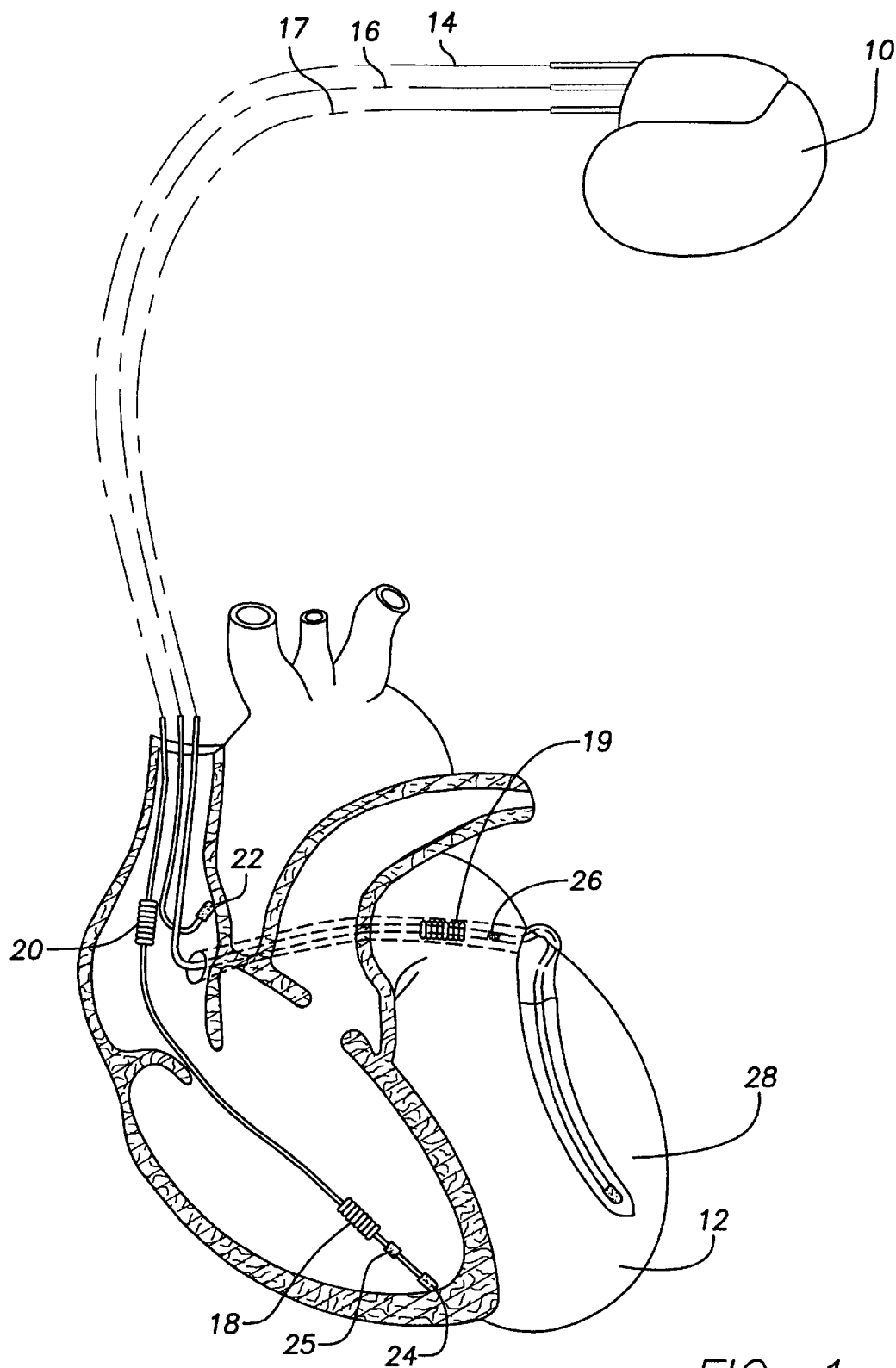
FIG. 1 illustrates an ICD coupled to a heart.

FIG. 1 illustrates a multi-chamber implantable stimulation device 10 which is capable of treating both fast and slow arrhythmias with stimulation therapy, including cardioversion, defibrillation, and pacing stimulation. While a multi-chamber device is shown, this is for illustration purposes only, and one of skill in the art could readily eliminate or disable the appropriate circuitry to provide a single-chamber or dual-chamber stimulation device capable of treating one or two chambers with cardioversion, defibrillation and pacing stimulation.

To provide right atrial chamber pacing stimulation and sensing, the stimulation device 10 is shown in electrical communication with a patient's heart 12 by way of an implantable atrial lead 16 having an atrial tip electrode 22 and (optionally) an atrial ring electrode (not shown) which typically is implanted in the patient's atrial appendage.

The stimulation device 10 is also shown in electrical communication with the patient's heart 12 by way of an implantable ventricular lead 14 having, in this embodiment, a ventricular tip electrode 24, a ventricular ring electrode 25, a right ventricular (RV) coil electrode 18, and an SVC coil electrode 20. Typically, the ventricular lead 14 is transvenously inserted into the heart 12 so as to place the RV coil electrode 18 in the right ventricular apex, and the SVC coil electrode 20 in the superior vena cava. Accordingly, the ventricular lead 14 is capable of receiving cardiac signals, and delivering stimulation in the form of pacing and shock therapy to the right ventricle.

To sense left atrial and ventricular cardiac signals and to provide left chamber pacing therapy, the stimulation device 10 is coupled to the "coronary sinus" lead 17 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. For a complete description of a coronary sinus lead, see U.S. patent application Ser. No. 09/457,277, "A Self-Anchoring, Steerable Coronary Sinus Lead" (Pianca et. al), and U.S. Pat. No. 5,466,254, "Coronary Sinus Lead with Atrial Sensing Capability" (Helland), which patents are hereby incorporated herein by reference.

The pacing/sensing/defibrillation leads detect IEGM signals at various locations within the heart for transmission to the ICD for analysis therein. As shown, the sensing/pacing locations are right atrium (high septal wall), left atrium (distal coronary sinus), right ventricular apex and left ventricle (via a cardiac vein). Among other functions, the ICD analyzes IEGM signals from these sensing sites to determine whether atrial or ventricular tachyarrhythmia is occurring and whether cardioversion/defibrillation therapy is required. Low energy therapy (e.g. anti-tachycardia pacing) may then be delivered via the sensing/pacing leads to the appropriate location(s). High energy cardioversion/defibrillation pulses may be delivered to the atria via the atrial shocking coils 19 and 20, or to the ventricles via the ventricular shocking coil 18 with several shock vectors possible using the shocking coils and ICD case in various configurations.

Figure 2:
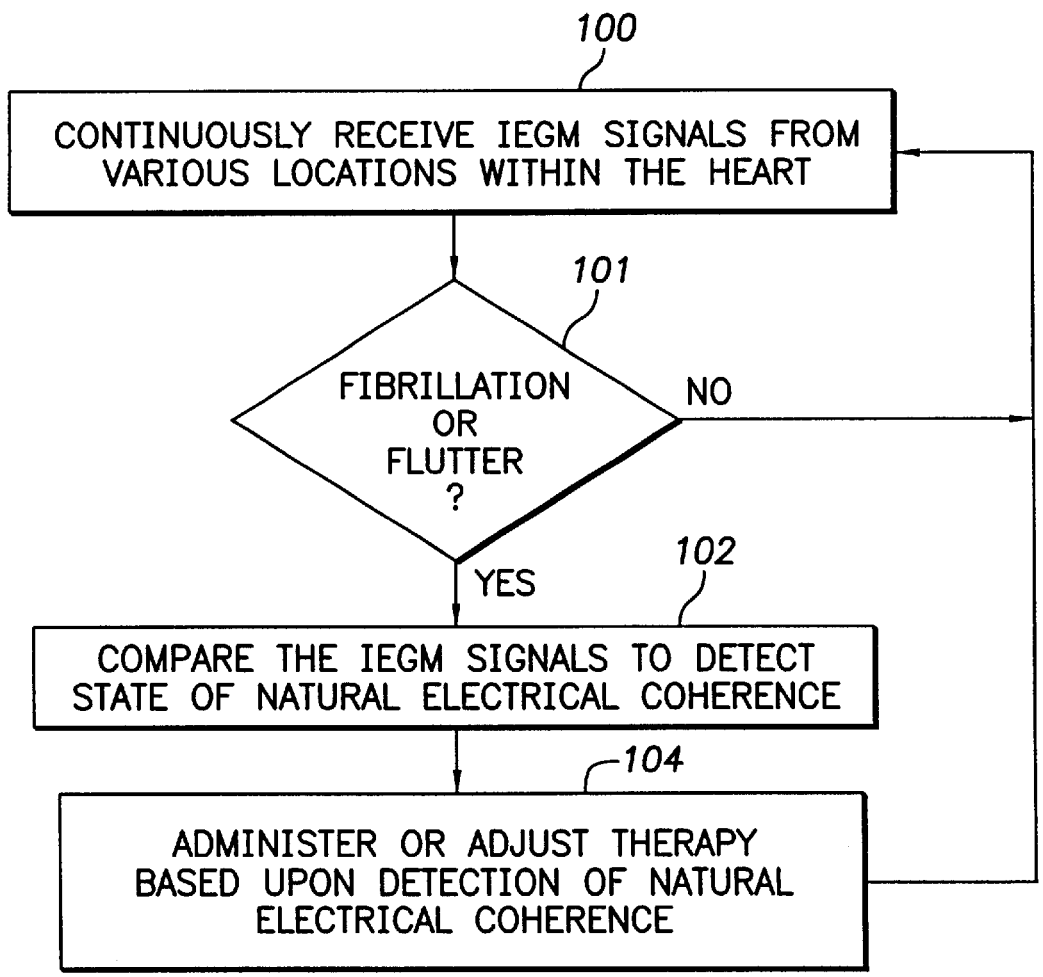
FIG. 2 illustrates a sequence of steps performed by the ICD of FIG. 1 for administering electrical therapy to the heart wherein the therapy is administered based upon detection of periods of natural electrical coherence.

Referring now to FIG. 2, an overview of the technique for administering therapy based upon detection of natural electrical coherence as performed by an ICD will now be described. Initially, at step 100, the ICD continuously receives IEGM signals from a set of sensing locations within the heart. In one example, the set of locations is all within the left atria of the heart. In another example, the locations are split among the left and right ventricles. At step 101, the ICD decides if atrial fibrillation (AFIB) or atrial flutter (AFL) exists in the locations being sensed. If yes, at step 102 the ICD compares the IEGM signals from the sensing locations to determine whether a period of natural electrical coherence has occurred.

Coherence is detected, for example, by comparing the relative timing of events sensed at the various sensing locations to one another. If the events are synchronized with one another, coherence has occurred. In another example, coherence is detected by identifying some minimum number of synchronized events occurring within a pre-determined period of time.

In one example, coherence may be based upon voltage threshold crossings (as will be described in more detail below in conjunction with FIG. 3B). Briefly, an electrically detectable event originating in the atria during flutter or fibrillation is referred to as an $F_A$-wave. An electrically detectable event originating in the ventricles during flutter or fibrillation is referred to as an $F_V$-wave.

In yet another example (described in more detail in conjunction with FIG. 3C), coherence is detected by evaluating the IEGM signals from the various sensing locations over a common time interval to detect some common feature. The evaluation consists of the measurement of some feature or combination of features of the time-limited signals from the multiple sites such as point-by point amplitude, frequency content or average slope. The measurements are compared against each other and/or against a reference parameter or template. When a minimum number of comparisons in a certain time interval reveal the measurements to be in agreement with each other (and/or in agreement with the reference) within acceptable limits, coherence is deemed to have occurred.

Once coherence has been determined, the ICD then adjusts or administers therapy, at step 104, based upon the coherence. For example, if the heart is subject to atrial fibrillation, the ICD administers a cardioversion shock to the atria at a time relative to coherence. In this regard, the pulse may be administered during the state of coherence or perhaps shortly thereafter or perhaps only after some number of coherence states have been detected. Optimal timing of the cardioversion shock relative to the natural electrical coherence is determined based upon routine experimentation and may depend upon other factors such as the current state of the ventricles. Other circumstances wherein it may be appropriate to administer or adjust therapy based upon detection of coherence include the administration of defibrillation shocks to the ventricles to terminate ventricular fibrillation, or the adjustment of the timing of pacing pulses to the heart, such as anti-tachycardia pacing pulses.

FIG. 3A illustrates a period of natural electrical coherence between the left and right atria as represented by intracardiac electrogram (IEGM) signals detected from the left and right atria during a period of time wherein $F_A$-waves are discernable. More specifically, FIG. 3A illustrates a left atrial IEGM signal 110 and a right atrial IEGM signal 112, each being representative of voltages as a function of time. (The IEGM signals illustrated in FIG. 3A are stylized signals, wherein each $F_A$-wave is represented by a discrete spike. The stylized spikes of FIG. 3A are provided to illustrate the concept of coherence. In practice, IEGM signals do not appear as uniform spikes.) Each IEGM signal includes a generally chaotic sequence of naturally occurring $F_A$-waves representative of muscular contractions within the atria. During a time period 114, the left and right atrial IEGM signals are more or less aligned with one another, i.e., $F_A$-waves of the left atria are generally aligned with $F_A$-waves of the right atria. This period of alignment is representative of a period of natural electrical coherence between the left and right atria. Other portions of the atrial IEGM signals, denoted 116, represent periods of time wherein the atria are not naturally electrically coherent. As can be seen, the $F_A$-waves within periods of non-coherence are generally not aligned with one another. It is believed that a generally higher atrial DFT occurs during periods of non-coherence 116.

FIG. 3B illustrates periods of natural electrical coherence between two locations within the atria during a period of fibrillation. More specifically, FIG. 3B illustrates IEGM signals 120 and 122 detected at sites A1 and A2, respectively, within the atria. The exemplary IEGM signals of FIG. 3B are representative of a period of atrial fibrillation/flutter. Time periods 126 identified by dashed ovals represent periods of natural electrical coherence between locations A1 and A2. More specifically, in this figure, coherence is defined by concurrent IEGM voltage threshold crossings at the two sites. Hence, a voltage threshold crossing is an $F_A$-wave. Graphs showing voltage threshold crossing detections are also provided within the figure. Other portions of the atrial IEGM signals, denoted 128, represent periods of time wherein the two locations are not naturally electrically coherent.

Figure 3C:
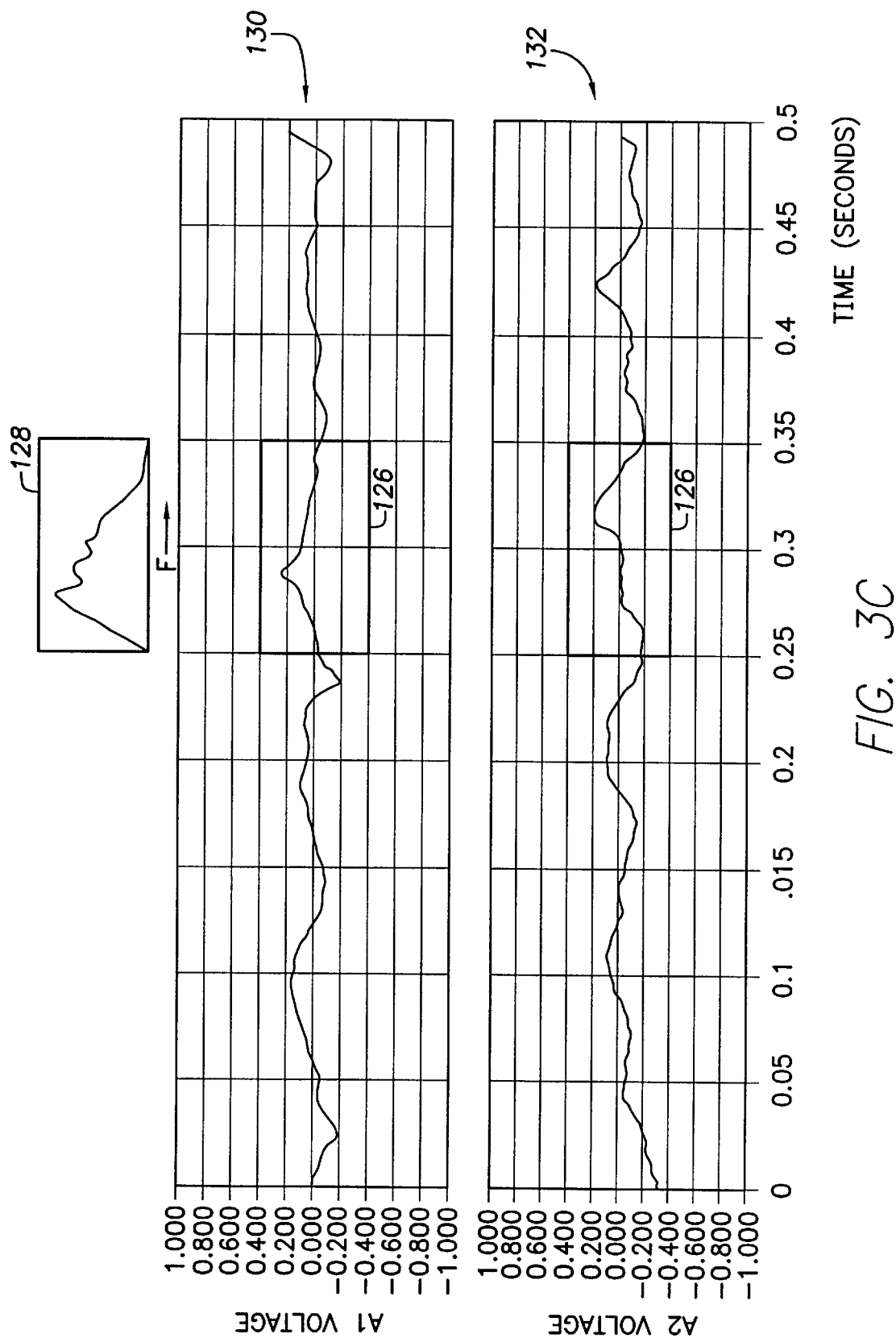
FIG. 3C illustrates left and right atrial IEGM signals along with an atrial frequency template representative of atrial IEGM frequency components occurring during a period of coherence.

FIG. 3C illustrates periods of natural electrical coherence between two locations within the atria as determined based upon frequency content of a portion of the signals. More specifically, FIG. 3C illustrates IEGM signals 130 and 132 detected at sites A1 and A2, respectively, within the atria. Time period 126 represents a common time interval in which the frequency content of the signals are extracted for comparison against a pre-determined template 128 representative of the expected frequency content of atrial IEGM signals during a period of natural electrical coherence. Briefly, the electrical signals captured within time interval 126 are processed to extract the frequency components therein using, for example, a conventional frequency extraction method such as the Fast Fourier Transform (FFT). The frequency components extracted during the time interval are then compared with the frequency components stored in the template, which are, as noted, representative of expected frequency components during a period of coherence. If the frequency components of the common time interval substantially match those of the template, a conclusion is drawn that coherence has occurred. Otherwise, a conclusion is drawn that the atria are not electrically coherent.

In the alternative, the frequency components extracted during the common time intervals within the left and right atria may be compared with one another, rather than against a template. In that embodiment, coherence is identified if the frequency components of the left atrium substantially match those of the right atrium. As noted above, numerous other features detectable within common time intervals may be analyzed to determine whether the atria are coherent. For each type of feature, routine experimentation may be performed to determine which features are representative of periods of natural electrical coherence so that the ICD can be programmed accordingly. Two or more different features may be analyzed to detect coherence. For example, the ICD may analyze both frequency components and amplitude components of the IEGM signals and identify periods of coherence only when the separate features both indicate a high degree of coherence. As can be appreciated, a wide range of combinations of these techniques may be employed consistent with the general principles of the invention.

Figure 4:
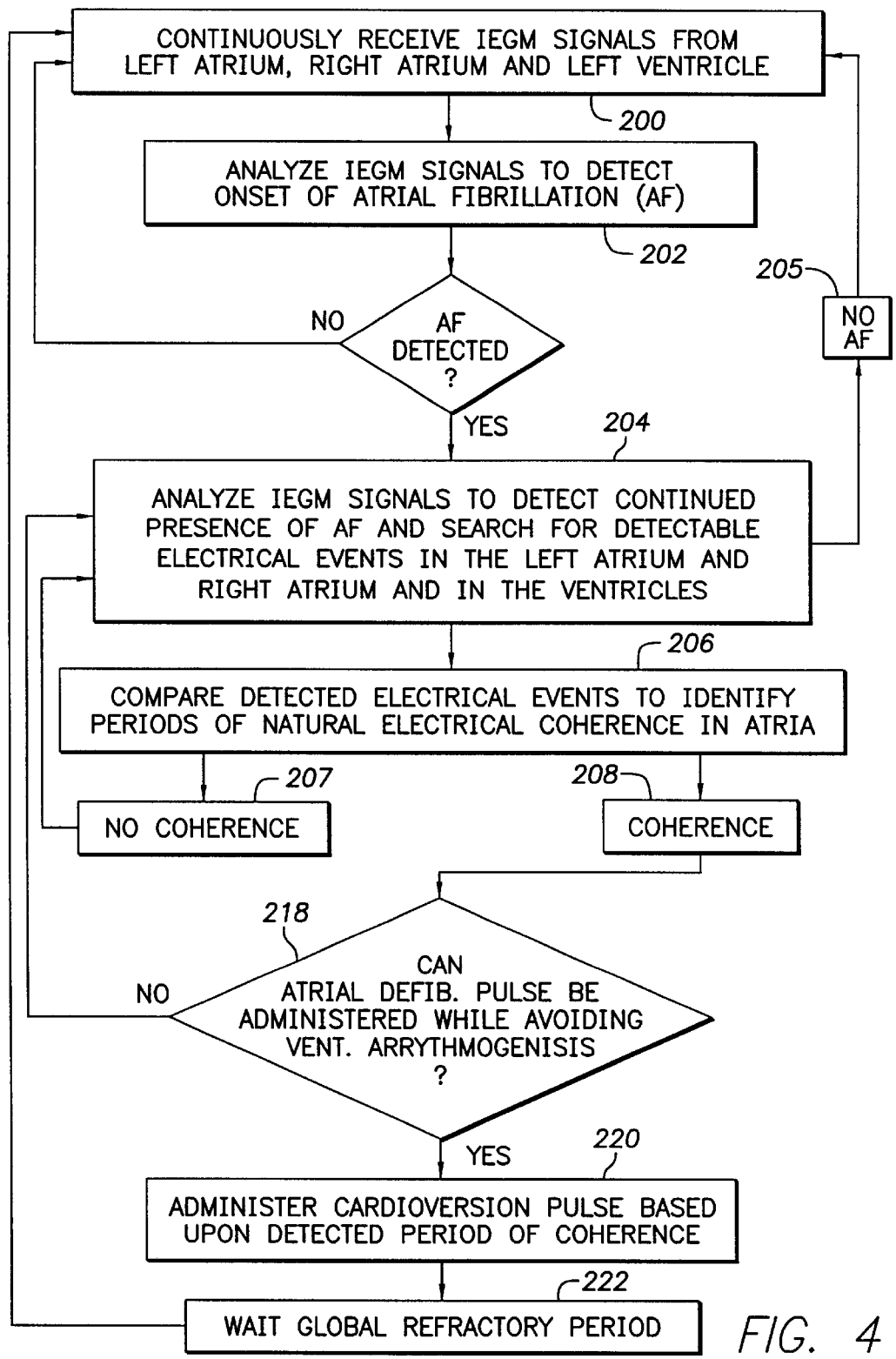
FIG. 4 illustrates a sequence of steps performed by the ICD of FIG. 1 for defibrillating the atria of the heart.

Referring now to FIG. 4, details of a particular technique for exploiting natural electrical coherence will now be described. The particular technique of FIG. 4 relates to the administration of cardioversion pulses to the atria to terminate atrial fibrillation. Initially, at step 200, the ICD continuously receives IEGM signals from the left and right atria and from the left ventricle and, at step 202, analyzes the IEGM signals to detect the onset of AF. If AF is detected then, at step 204, the ICD analyzes the IEGM signals to detect the continued presence of AF and $F_A$-waves in the left and right atria. If AF is no longer present, step 205, execution returns to step 200. As part of the $F_A$-wave detection process, the ICD also tracks R-waves. (Note that, with the heart subject to atrial fibrillation rather than ventricular fibrillation, R-waves are detectable within the ventricles and techniques relying on detection of other types of $F_V$-waves are not required.) In any case, the R-waves are tracked so as to permit the cardioversion pulses to be administered at times selected to prevent ventricular arrhythmogenesis. Detection of R-waves also permits the ICD to verify that the $F_A$-waves are "true" $F_A$-waves representative of electrical activity originating in the atria and not merely the result of a far-field R-wave. A technique for distinguishing electrical activity originating in the atria from far field R-waves is described in U.S. Pat. No. 6,516,225, entitled "System and Method for Distinguishing Electrical Events Originating in the Atria from Far-Field Electrical Events Originating in the Ventricles as Detected by an Implantable Medical Device", assigned to the assignee of the present invention, and incorporated by reference herein. In the following, it is assumed that far field R-waves have been filtered out by the ICD and that all $F_A$-waves are true $F_A$-waves.

At step 206, the ICD compares the temporal alignment of the $F_A$-waves to determine whether the left and right atria are in a state of natural electrical coherence. In this regard, the ICD tracks a time delay, if any, occurring between the detection of $F_A$-waves in the left and right atrial IEGM signals. If the time delay between $F_A$-waves of the left and right atrial IEGM signals is less than a pre-determined threshold, the ICD concludes that the atria is in state of electrical coherence. If the time delay between $F_A$-waves of the left and right atrial IEGM signals is greater than the pre-determined threshold, the ICD instead concludes that the atria are not electrically coherent. Insofar as the detection of the $F_A$-waves is concerned, an IEGM signal, such as the one shown in FIG. 3B, is analyzed using the aforementioned detection techniques. Alternatively, techniques not requiring detection of $F_A$-waves by voltage threshold crossing can be employed to detect atrial coherence such as the aforementioned technique involving evaluation of the IEGM signals within common time intervals to detect point-by point amplitude, frequency content or average slope.

If coherence is not detected, step 207, execution returns to step 204 to continue to search for coherence. If coherence is detected, step 208, execution proceeds to step 218, wherein the ICD then determines whether an atrial cardioversion pulse can be administered while avoiding ventricular arrhythmogenesis, i.e. while avoiding the triggering of ventricular fibrillation or other ventricular dysrhythmia. If ventricular arrhythmogenesis can be avoided, the pulse is administered at step 220. Actual timing of the pulse relative to the state of natural electrical coherence may depend upon the current state of the ventricles and upon other factors such as the manner by which the coherence was detected. In some cases it may be optimal to administer the pulse as early as possible during the period of coherence; in other cases it may be optimal to wait until coherence has just ended. Routine experimentation is employed to determine the optimal time for administering the pulse based upon the circumstances. The ICD is programmed to administer the pulse at the optimal time.

After a pulse has been administered, the ICD then begins tracking a global refractory period at step 222. Execution does not return to step 200 until completion of the global refractory period. In this manner, the ICD is prevented from administering any further cardioversion pulses until completion of the global refractory period. If, following a return to step 200, AF is again detected at step 202, indicating that AF was not properly terminated by the cardioversion pulse, then the various steps of FIG. 4 are repeated to possibly administer additional cardioversion pulses. Preferably, the energy level of each successive cardioversion pulse is increased to help insure proper defibrillation of the atria. Although not specifically shown in FIG. 4, the ICD preferably employs a timer configured such that, if coherence is not detected within a predetermined period of time, the ICD administers the cardioversion pulse without regard to electrical coherence (though the ICD still ensures that the cardioversion pulse is administered so as to avoid ventricular arrhythmogenesis). This prevents any undue delay in administering the cardioversion pulse.

If, at step 218, ventricular arrhythmogenesis can not be avoided with reasonable certainty, no cardioversion pulse is administered and execution returns to step 204 to search for a subsequent period of coherence wherein the pulse can be safely administered. Insofar as the avoidance of ventricular arrhythmogenesis is concerned, a variety of techniques for timing cardioversion pulses to avoid ventricular arrhythmogenesis may be exploited. One technique is to detect an intrinsic R-wave and then administer the cardioversion pulse during a ventricular refractory period subsequent thereto. Another technique involves the triggering of an R-wave upon detection of coherence to ensure that a refractory period is available.

Figure 5:
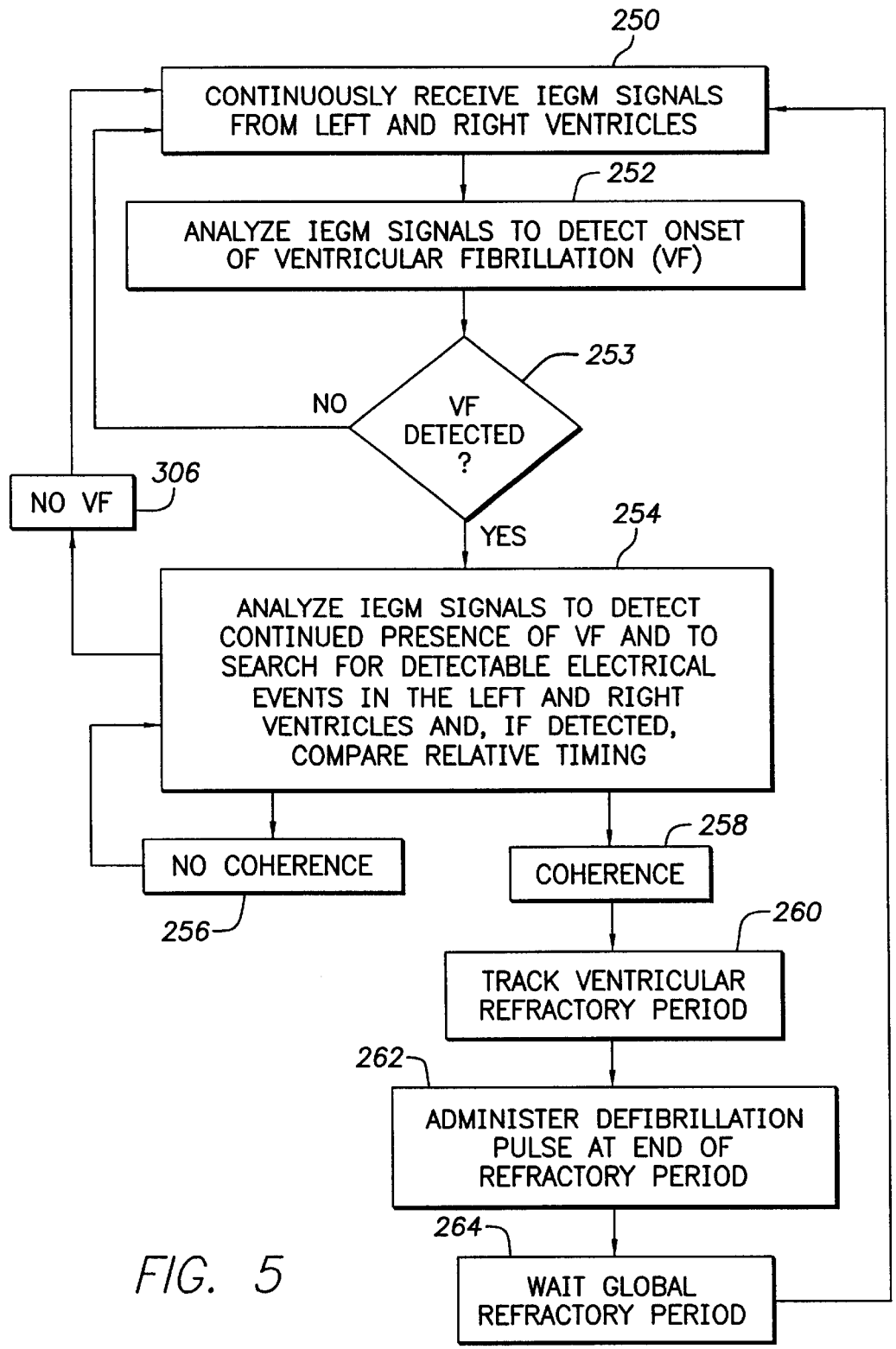
FIG. 5 illustrates a sequence of steps performed by the ICD of FIG. 1 for defibrillating the ventricles of the heart.

Referring to FIG. 5, the details of a technique for administering defibrillation therapy to the ventricles of the heart performed by the ICD will now be summarized. Many of the steps set forth in FIG. 5 are similar to steps already described with reference to FIG. 4 and, hence, the steps will not be described in great detail.

Briefly, within steps 250 and 252, the ICD continuously receives IEGM signals from the left and right ventricles and analyzes the signals to detect the onset of VF. If it is determined that VF is no longer present at step 253, execution returns to step 250.

If VF is detected (at step 253), then the ICD (at step 254) analyzes the IEGM's for the continued presence of VF, searches for $F_V$-waves within the left and right ventricles and compares the relative timing of the $F_V$-waves to determine whether the left and right ventricles are electrically coherent. If the $F_V$-waves are not aligned with one another, then the ICD determines that there is no coherence, step 256. If, on the other hand, the $F_V$-waves are found to be aligned with one another, then the ICD determines that the ventricles are coherent, step 258.

Assuming that the ventricles are coherent, execution proceeds to step 260 to determine the ventricular refractory period, and then the ICD administers a ventricular defibrillation pulse at step 262. As with atrial cardioversion described above, actual timing of the ventricular defibrillation pulse relative to the state of natural electrical coherence may depend upon various factors such as the manner by which the coherence was detected. Routine experimentation is employed to determine the optimal time for administering the pulse based upon the circumstances. The ICD is programmed to administer the pulse at the optimal time.

After the ventricular defibrillation pulse has been administered, the ICD then waits a global refractory period, step 264, before returning to step 250 to analyze further IEGM signals to determine whether the ventricles are still fibrillating. If the first pulse did not terminate fibrillation, the sequence of steps are repeated and additional pulses are administered with all available remaining electrical energy within the ICD in an attempt to terminate the fibrillation.

Thus, FIG. 5 sets forth a method whereby an ICD times a defibrillation pulse based upon detection of natural electrical coherence in the ventricles. Although not specifically shown in FIG. 5, the ICD preferably employs a time-out period such that, if coherence is not detected within a predetermined period of time, the ICD administers the defibrillation pulse without regard to electrical coherence. This prevents any undue delay in administering the defibrillation pulse.

The techniques of the invention have been described thus far primarily with reference to exemplary method embodiments. Each method step described herein and illustrated in the drawings also represents an apparatus element for performing the method step. The apparatus elements may be referred to herein as a unit for or a means for performing the method step.

Figure 6:
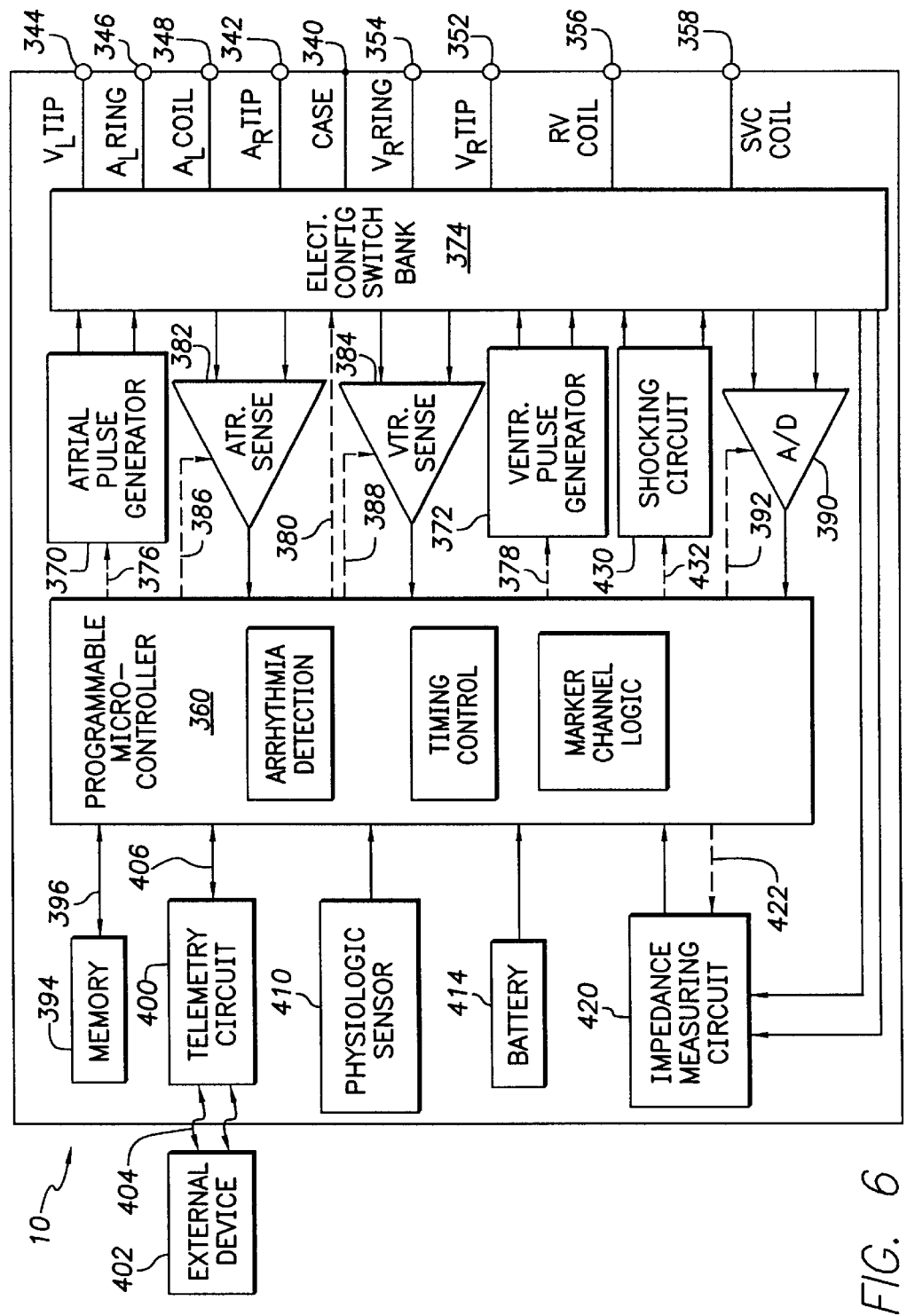
FIG. 6 illustrates a system for use within an ICD or pacemaker for administering therapy based upon detection of a period of natural electrical coherence in accordance with the invention.

FIG. 6 illustrates internal components of an ICD that configured to perform the method described above in connection with FIGS. 1, 2, 4 and 5.

The housing 340 for the stimulation device 10, shown schematically in FIG. 6, is often referred to as the "can", "case" or "case electrode" and may be programmably selected to act as the return electrode for all "unipolar" modes. The housing 340 may further be used as a return electrode alone or in combination with one or more of the coil electrodes, 18, 19 or 20, for shocking purposes. The housing 340 further includes a connector (not shown) having a plurality of terminals, 342, 344, 346, 348, 352, 354, 356, and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 22.

To achieve left chamber sensing, pacing and shocking, the connector includes at least a left ventricular tip terminal ($V_L$ TIP) 344, a left atrial ring terminal ($A_L$ RING) 46, and a left atrial shocking terminal ($A_L$ COIL) 348, which are adapted for connection to the left ventricular ring electrode 25, the left atrial electrode 26, and the left atrial coil electrode 19, respectively.

To support right chamber sensing, pacing and shocking, the connector further includes a right ventricular tip terminal ($V_R$ TIP) 352, a right ventricular ring terminal ($V_R$ RING) 354, a right ventricular shocking terminal (RV COIL) 356, and an SVC shocking terminal (SVC COIL) 358, which are adapted for connection to the right ventricular tip electrode 24, right ventricular ring electrode 25, the RV coil electrode 18, and the SVC coil electrode 20, respectively.

At the core of the stimulation device 10 is a programmable microcontroller 360 which controls the various modes of stimulation therapy and performs, in combination with other units of the ICD, the methods described above in connection with FIGS. 2–5. As is well known in the art, the microcontroller 360 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the present invention. Rather, any suitable microcontroller 360 may be used that carries out the functions described herein. The use of microprocessor-based control circuits for performing timing and data analysis functions is well known in the art. As shown in FIG. 6, an atrial pulse generator 370 and a ventricular pulse generator 372 generate pacing stimulation pulses for delivery by the atrial lead 16 and the ventricular lead 14, respectively, via a switch bank 374. The pulse generators, 370 and 372, are controlled by the microcontroller 360 via appropriate control signals, 376 and 378, respectively, to trigger or inhibit the stimulation pulses. The microcontroller 360 further includes timing circuitry that controls the operation of the stimulation device timing of such stimulation pulses, that is well known in the art.

The switch bank 374 includes a plurality of switches for switchably connecting the desired electrodes to the appropriate I/O circuits, thereby providing complete electrode programmability. Accordingly, the switch bank 374, in response to a control signal 380 from the microcontroller 360, determines the polarity of the stimulation pulses (e.g., unipolar or bipolar) by selectively closing the appropriate combination of switches (not shown) as is known in the art.

An atrial sense amplifier 382 and a ventricular sense amplifier 384 are also coupled to the atrial and ventricular leads, 16 and 14, respectively, through the switch bank 374 for detecting the presence of cardiac activity. The switch bank 374 determines the "sensing polarity" of the cardiac signal by selectively closing the appropriate switches, as is also known in the art. In this way, the clinician may program the sensing polarity independent of the stimulation polarity.

Each sense amplifier, 382 and 384, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers, 382 and 384, are connected to the microcontroller 360, which, in turn, inhibit the atrial and ventricular pulse generators, 370 and 372, respectively, in a demand fashion whenever cardiac activity is sensed in the respective chambers.

For arrhythmia detection is typically performed by the microcontroller 360, in conjunction with the atrial and ventricular sense amplifiers, 382 and 384, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 360 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the atrial and ventricular leads, 16 and 14, through the switch bank 374 to sample cardiac signals across any pair of desired electrodes.

The microcontroller 360 is further coupled to a memory 394 by a suitable data/address bus 396, wherein the programmable operating parameters used by the microcontroller 360 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 328 within each respective tier of therapy.

Advantageously, the operating parameters of the implantable device 10 may be non-invasively programmed into the memory 394 through a telemetry circuit 400 in telemetric communication with an external device 402, such as a programmer, transtelephonic transceiver, or a diagnostic system analyzer. The telemetry circuit 400 is activated by the microcontroller by a control signal 406. The telemetry circuit 400 advantageously allows intracardiac electrograms and status information relating to the operation of the device 10 (as contained in the microcontroller 360 or memory 394) to be sent to the external device 402 through the established communication link 404. In the preferred embodiment, the stimulation device 10 further includes a physiologic sensor 410. Such sensors are commonly called "rate-responsive" sensors. The physiological sensor 410 is used to detect the exercise state of the patient, to which the microcontroller 360 responds by adjusting the rate and AV Delay at which the atrial and ventricular pulse generators, 370 and 372, generate stimulation pulses. The type of sensor used is not critical to the present invention and is shown only for completeness.

The stimulation device additionally includes a battery 414, which provides operating power to all of the circuits shown in FIG. 6. For the stimulation device 10, which employs shocking therapy, the battery must be capable of operating at low current drains for long periods of time, and then be capable of providing high-current pulses (for capacitor charging) when the patient requires a shock pulse. The battery 414 must also have a predictable discharge characteristic so that elective replacement time can be detected. Accordingly, the present invention employs lithium/silver vanadium oxide batteries, as is true for most (if not all) such devices to date.

As further shown in FIG. 6, the ICD of the invention may include an impedance measuring circuit 420 which is enabled by the microcontroller 360 by a control signal 422. The impedance measuring circuit 420 is not critical to the present invention and is shown for only completeness.

The ICD detects the occurrence of an arrhythmia, and automatically applies an appropriate electrical shock therapy to the heart aimed at terminating the detected arrhythmia. To this end, the microcontroller 360 further controls a shocking circuit 430 by way of a control signal 432. The shocking circuit 430 generates shocking pulses of low (up to 0.5 Joules), moderate (0.5–10 Joules), or high energy (11 to 40 Joules), as controlled by the microcontroller 360. Such shocking pulses are applied to the patient's heart through at least two shocking electrodes, and as shown in this embodiment, using the RV and SVC coil electrodes, 18 and 20, respectively. In alternative embodiments, the housing 340 may act as an active electrode in combination with the RV electrode 18 alone, or as part of a split electrical vector using the SVC coil electrode 20 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Aspects of the invention may be embodied within software running within a programmable processor within the device or may be implemented as hard-wired logic within an application specific integrated circuit (ASIC) or the like.

Accordingly, and as one of skill in the art can appreciate, the present invention can be employed with the microcontroller system described in FIG. 6. Although described with respect to embodiments wherein natural electric coherence is detected by sensing IEGM signals at only one location within each chamber of the heart, the invention is also applicable to detecting natural electrical coherence based upon additional sensing locations. For example, IEGM signals may be sensed within N locations within each chamber of the heart wherein N is, for example, between 2 and 10. In those implementations, the cardioversion pulses are administered only if mutual coherence is detected among all of the IEGM signals from all of the sensing locations, or perhaps among some predetermined subset thereof. If coherence is determined based upon numerous sensing locations, the techniques described above may be modified as needed to accommodate the larger number of sensing locations. As can be appreciated, a wide variety of specific techniques, consistent with the general principles of invention, are applicable to defining and detecting natural electrical coherence so as to permit application of electrical pulses to the heart during the periods of coherence.

Also, the ICD or pacemaker may additionally be programmed to administer the pulse only after the occurrence of two or more periods of electrical coherence. To this end, the ICD or pacemaker counts each individual period of electrical coherence after the onset of fibrillation, then administers the electrical pulse only after a predetermined number of occurrences of coherence have been detected. The predetermined number may be, for example, between two and ten, inclusive. Typically, the predetermined number is programmed to be less for ventricular defibrillation than for atrial defibrillation. Also, as far as ICD's are concerned, preferably the aforementioned time-out counter is employed to prevent an undue delay in administering either type of cardioversion pulse such that, if the predetermined number of occurrences of coherence are not extended within the time-out period, the ICD administers the appropriate pulse without further delay.

The invention itself may be implemented within an ICD, pacemaker or other implantable medical device using conventional techniques. In this regard, the invention may be embodied within software running within a programmable processor within the device or may be implemented as hard-wired logic within an application specific integrated circuit (ASIC) or the like.

What have been described are various techniques for detecting natural electrical coherence and for adjusting or administering therapy based thereon. In general, the embodiments described herein are merely illustrative of the invention and should not be construed as limiting the scope of the invention, which is to be interpreted in accordance with the claims that follow.

What is claimed is:

1. A method for analyzing the electrical activity of the heart using an implantable medical device connected to a heart, the implantable medical device comprising a cardiac stimulating device, the method comprising the steps of:
    detecting atrial electrical signals from at least two separate atrial locations within the heart;
    comparing the atrial electrical signals to detect a period of natural atrial electrical coherence among the atrial electrical signals; and
    selectively administering therapy to the heart using the cardiac stimulating device with the therapy administered at a time selected based upon the period of natural atrial electrical coherence.

2. The method of claim 1, wherein the steps are performed while the heart is in a state of arrhythmia.

3. The method of claim 2, wherein the arrhythmia is atrial fibrillation.

4. The method of claim 3, wherein the step of selectively administering therapy comprises the step of administering at least one defibrillation or cardioversion pulse to the atria.

5. The method of claim 3, wherein the step of detecting atrial electrical signals from at least two separate atrial locations within the heart comprises the step of:
    detecting electrical signals from at least one location in the left atrium and from at least one location in the right atrium of the heart, or from at least two locations in either the right or left atrium.

6. The method of claim 1, wherein the step of detecting electrical signals from at least two separate atrial locations within the heart comprises the step of detecting IEGM signals.

7. The method of claim 1, wherein the step of comparing the atrial electrical signals to detect a period of natural electrical coherence comprises the steps of:
    identifying portions of the atrial electrical signals from the at least two separate atrial locations within the heart that correspond with one another;
    tracking time delays occurring between the corresponding portions of the atrial electrical signals to compare temporal alignment of the corresponding portions of the atrial electrical signals;
    comparing the time delays with a predetermined coherence-detection time period; and
    concluding that the heart is in a state of natural electrical coherence if the time delays are less than the predetermined coherence-detection time period.

8. The method of claim 1, wherein:
    the step of detecting atrial electrical signals from the at least two separate atrial locations within the heart comprises the step of detecting $F_A$-waves within the atria of the heart; and
    the step of comparing the atrial electrical signals to detect a period of atrial coherence comprises the step of identifying corresponding $F_A$-waves.

9. The method of claim 1, wherein the step of comparing the atrial electrical signals to detect a period of natural atrial electrical coherence comprises the steps of:
    identifying features of the atrial electrical signals within a common time interval;
    comparing the features from the at least two separate atrial locations with one another; and
    concluding that the heart is in a state of natural atrial electrical coherence if the features are substantially similar.

10. The method of claim 9, wherein the features are selected from a group including frequency content, point-by-point amplitude and average slope.

11. The method of claim 1, wherein the step of comparing the atrial electrical signals to detect a period of natural electrical coherence comprises the steps of:
    identifying features of the atrial electrical signals within a common time interval;
    comparing the features from the at least two separate atrial locations with a predetermined template representative of the features expected to occur during a period of natural atrial electrical coherence; and
    concluding that the heart is in a state of natural atrial electrical coherence if the features from the at least two separate atrial locations substantially match the features of the template.

12. The method of claim 1, wherein the step of selectively administering therapy to the heart at a time relative to the period of natural atrial electrical coherence is performed to administer an electrical pulse during the period of natural atrial electrical coherence.

13. A system for analyzing the electrical activity of the heart using an implantable medical device connected to a heart, the system comprising:
    means for detecting electrical signals at a plurality of separate locations within either the atria or the ventricles of the heart;
    means for comparing the electrical signals to detect a period of natural electrical coherence among the signals;
    the implantable medical device comprising a cardiac stimulating device; and
    the system additionally comprising means for selectively administering therapy to the heart using the cardiac stimulating device with the therapy administered at a time selected based upon the period of natural electrical coherence.

14. A system for analyzing the electrical activity of the heart using an implantable medical device connected to a heart, the system comprising:
    a cardiac electrical activity detection unit for detecting electrical signals at a plurality of separate locations within either the atria or the ventricles of the heart;
    a natural electrical coherence detection unit for comparing the electrical signals to detect a period of natural electrical coherence among the signals;

the implantable medical device comprising a cardiac stimulating device; and the system additionally comprising an electrical therapy generator for selectively administering therapy to the heart using the cardiac stimulating device with the therapy administered at a time selected based upon the period of natural electrical coherence.

15. A method for analyzing the electrical activity of the heart using an implantable medical device connected to a heart, the method comprising the steps of:

detecting atrial electrical signals from at least two separate atrial locations within the heart; and comparing the atrial electrical signals to detect a period of natural atrial electrical coherence among the atrial electrical signals;

wherein the step of comparing the electrical signals to detect a period of natural electrical coherence comprises the steps of:

determining the first derivative of each signal with respect to time of the amplitude signals;

comparing the first derivative of each signal with some threshold;

determining the amount of time between threshold crossings of the first derivative of each signal;

comparing the amount of time with a predetermined coherence detection time period; and determining that the heart is in a state of natural electrical coherence if the amount of time is less than the predetermined coherence detection period.

* * * * *